United States Patent [19]

Kurtz et al.

[11] 4,433,973
[45] Feb. 28, 1984

[54] REUSABLE TUBE CONNECTOR ASSEMBLY

[75] Inventors: Leonard D. Kurtz, Woodmere; Joseph M. LiCausi, Port Jefferson Sta., both of N.Y.

[73] Assignee: BioResearch Inc., Farmingdale, N.Y.

[21] Appl. No.: 338,834

[22] Filed: Jan. 12, 1982

[51] Int. Cl.³ .................... A61M 5/14; A61M 1/02
[52] U.S. Cl. ..................................... 604/403; 604/905
[58] Field of Search ................... 604/4, 7, 905, 283, 604/326, 403; 285/3, 21, 331, 260, 423, DIG. 2, 285/DIG. 16, 360, 361, 376, 396, 401, 402

[56] References Cited

U.S. PATENT DOCUMENTS

| 2,907,591 | 10/1959 | Gulick | 285/361 X |
| 3,768,476 | 10/1973 | Raitto | 285/331 X |
| 3,976,311 | 8/1976 | Spendlove | 604/283 X |
| 4,214,779 | 7/1980 | Losell | 285/423 X |
| 4,256,106 | 3/1981 | Shoor | 604/905 X |
| 4,346,704 | 8/1982 | Kulle | 604/905 X |
| 4,354,490 | 10/1982 | Rogers | 604/905 X |
| 4,366,816 | 1/1983 | Bayard et al. | 604/403 |

Primary Examiner—C. Fred Rosenbaum
Assistant Examiner—Michelle Lester
Attorney, Agent, or Firm—Larson and Taylor

[57] ABSTRACT

A two-part connector assembly for connecting two tubes which prevents the entry of contaminates in the tubes during use and subsequent reuse of one part is disclosed. The connector assembly includes a reusable first connector member having an elongate housing and a sterile inner tubing located inside the housing. A reusable second connector member is also provided and includes an elongate housing, a sterile inner tubing located inside of the housing, and a sterile cover tubing located around the sterile inner tubing and also located inside of the housing. A connecting means is provided for holding the first connector member and the second connector member together such that no contaminates reach the inner tubing of either housing during use. The connector members can be reused as no contaminates reach the inner tubing of the reused connector member as well. Preferably, each connector member is integrally formed of a rigid material except for the cover tubing of the second connector member which is made of a flexible material. The assembled connector assembly has no longitudinal gaps between the first connector member and the second connector member through which contaminates can reach the inner tubings and the connector members cannot be inadvertently pulled apart.

11 Claims, 6 Drawing Figures

4,433,973

REUSABLE TUBE CONNECTOR ASSEMBLY

FIELD OF THE INVENTION

The present invention relates generally to a connector for two tubes or the like and more particularly to a connector assembly which prevents the entry of contaminates in the tubes during use and subsequent reuse of the connector assembly.

BACKGROUND OF THE INVENTION

Sterile fluid couplers or connectors have many uses such as the transfer of fluids used in cell culture systems, the collection and/or delivery of blood and blood components, the handling of kidney dialysis fluids, and the administration of parenteral solutions. In many such cases, it is desirable that the tubing or conduits used in the apparatus for dispensing or transferring of the fluids be provided with a quick disconnect or quick change coupler so that the tubing can rapidly be connected and disconnected, especially in an emergency or life-saving situation. Maintenance of sterility and the prevention of microbial contamination is a critical consideration in the use of the couplers.

Numerous such quick connect couplers have been developed and disclosed in the prior art. For example, in U.S. Pat. No. 3,394,954 (Sarns), a quick change tube coupling device has a first molded plastic tube connector which telescopically engages a second tube connector. The two tube connectors are locked together by a suitable means. While such a connector can be initially sterilized, after disconnection sterility of the coupling device is lost.

Other fluid couplers, as illustrated for example in U.S. Pat. Nos. 4,004,586 (Christensen et al), 4,022,205 (Tenczar), and 4,187,846 (Lolachi et al), have internal protective membranes of one sort or another which act as barriers against contamination of the coupling unit before and during use. It has also been suggested in the prior art, for example, in U.S. Pat. Nos. 3,667,781 (Holbrook) and 4,149,534 (Tenczar) to cover a chamber common to two tubes to fluidly connect the tubes. Despite the advantages of these devices, sterile reuse of the connecting devices is not possible.

In order to reduce contamination during periods of connection and also when the tubing is disconnected, it has been disclosed in U.S. Pat. No. 3,976,311 (Spendlove) to provide a tubing connector having first and second telescopically received parts. Mating closure parts are attached to each tubing connector part to plug the part and maintain internal sterility during disconnection. Both telescoping parts have inner tubing which telescopically receive each other. It has also been disclosed in U.S. Pat. No. 3,768,476 (Raitto) to provide a tube coupler with internal sealing surfaces which maintain internal sterility after disconnection. It has also been disclosed in the prior art in U.S. Pat. No. 4,253,684 (Tolbert et al) to maintain sterility during disconnection and subsequent reconnection of a tubular connector by passing sterile air over the parts during this procedure.

SUMMARY OF THE INVENTION

The present invention provides a reusable tube connector assembly for connecting two tube or the like which prevents the entry of contaminants in the tubes during use and a subsequent reuse of one part of the connector assembly. While the connector assembly of the present invention can be used in a variety of situations, one such situation is in connection with an autotransfusion device such as disclosed in U.S. patent application Ser. No. 290,666 filed Aug. 5, 1981, entitled "Disposable Autotransfusion Device". This application is assigned to the same assignee as the present application and is herein incorporated by reference. The autotransfusion device disclosed in this application is used to collect blood from a patient and to return this blood to the same patient. In order to collect the blood, a thoracotomy tube leads from the patient to the blood collection bag of the autotransfusion device. The blood collection bag of the autotransfusion device is also fluidly connected by an aspirator tube to a suitable source of negative pressure such as an underwater drainage device disclosed in U.S. Pat. Nos. 3,363,626 and 3,363,627. After one blood bag is filled, it is often desirable to attach a new blood bag to the two tubes or to connect the two tubes together so that the liquid flowing through the thoracotomy tube is deposited in the underwater drainage device. In order to connect the thoracotomy tube and the aspirator tube together, a connector of some type must be provided. However, it is imperative that the sterility of the thoracotomy tube and the aspirator tube be maintained at all times whether connected together or to the autotransfusion device.

With the present invention, the autotransfusion device is provided with the two necessary tubes, each of which has one part or the other part of a two part connector assembly attached thereto. The thoracotomy tube and the aspirator tube are then provided with a mating part of a connector assembly for connection to the other part of the appropriate tube of the autotransfusion device. In this manner, the autotransfusion device is easily and quickly attachable to the aspirator tube and the thoracotomy tube. Then, when the blood bag of the autotransfusion device is filled, the autotransfusion device is easily and quickly disconnected from the thoracotomy and aspirator tubes and the thoracotomy and aspirator tubes are easily and quickly connected to each other as their ends contain mating connecting members of the connector assembly of the present invention. It should be appreciated that with the connector assembly of the present invention, sterility of the thoracotomy tube and aspirator tube is maintained during connection of the autotransfusion device and subsequent reconnection to each other. It should also be appreciated that the two connector members provided on the ends of the tubes of the autotransfusion device can similarly be connected together to maintain the sterility of the liquid collected in the autotransfusion device.

According to the present invention, the connector assembly includes two reusable connector members. A first connector member includes an elongate housing with an opening in one end. A bore is provided through the elongate housing and an adapter is located at the other end of the housing around the bore. A sterile inner tubing is provided around the bore and inside of the first housing. The sterile inner tubing is spaced inwardly from the end of the housing and from the surrounding portion of the housing. The second connector member includes an elongate housing provided with an elongate opening which is sized to telescopically receive the housing of the first connector member. A bore through the housing, an adaptor on the end of the housing, and a sterile inner tubing is similarly provided in the second housing. Covering the sterile inner tubing of the second housing is a cover tubing which is also spaced inwardly from the end of the housing and from the adjacent surrounding portion. This cover tubing is sized to telescopically receive a portion of the inner tubing of the first housing. A connecting means is also provided for separably holding the two connector members together with a portion of the first housing telescopically located inside of a portion of the second housing and a portion of the inner tubing of the first housing telescopically located inside of the cover tubing and adjacent to the inner tubing of the second housing. This connecting means is preferably the friction fit between the cover tubing and the inner tubing of the first housing. With this construction, after disconnection and a subsequent reuse of one of the connector members with a mating connector member, the sterility of the inner tubing of the reused and new connector member is maintained.

It is a feature of the present invention that the diameter of the elongate opening and the location of the end of the cover tubing of the second connector member are designed to prevent the end of the housing of the first connector member from touching and thereby contaminating the sterile cover tubing of the second connector member. Thus, as the housing of the first connector member is inserted into the elongate opening of the second connector member, no matter what the initial angle of insertion, the housing of the first connector member cannot contact and contaminate the cover tubing of the second connector member. In this manner, the sterility of the inner tubing of a connector assembly is provided during use and the sterility of a subsequently reused and a new connector member is assured.

In the preferred embodiment of the present invention, the elongate housing, adaptor, and inner tubing of each connector member are integrally formed of a relatively rigid material. The cover tubing is then attached to one housing and is made of a relatively flexible material. Preferably, the end of the first housing contacts the second housing, and the two inner tubes contact each other when the connector assembly is operational. In this manner, no longitudinal gap exists between the connector members through which contaminants might pass and a smooth and uninterrupted flow conduit is provided for the conducted liquid. A stop means is also provided which prevents inadvertent disengagement of the connector members. This stop means includes a peg projecting from one housing which is received in an exit slot in the other housing. The slot has a transverse slot portion so that a relative rotation of the two housings is necessary for disengagement (and engagement). In the preferred embodiment of the invention, the housing, adapter, inner tubing and cover tubing of each connector member have a circular shaped cross section.

Additional features and advantages of the present invention will be apparent from a consideration of the following detailed description of the preferred embodiment of the invention in connection with the accompanying drawings.

DETAILED DESCRIPTION OF THE PREFERRED EMBODIMENT

Figure 4:
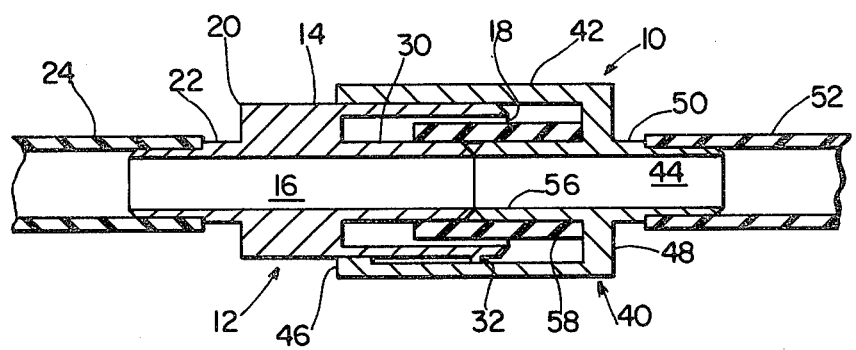
FIG. 4 is a cross-sectional plan view showing the two connector members in the connected position.

With reference now to the drawings in which like numerals represent like elements throughout the several views, a first, male connector member 12 of connector assembly 10 is depicted in FIGS. 1, 3, 4, and 6. Connector member 12 includes an elongate housing 14 through which a bore 16 coaxially extends. Housing 14 has a proximal end 18, a distal end 20 and a knurled portion 21. Located coaxially with bore 16 at distal end 20 is an adapter 22 to which a suitable tube 24 as shown in FIG. 4 is attached. Adapter 22 is sized to receive whatever sized tube is to be connected thereto.

Housing 14 also includes an annular opening 28 at proximal end 18. Located in annular opening 28 is a sterile inner tubing 30. Inner tubing 30 is coaxially mounted about bore 16. As shown best in FIGS. 1 and 3, inner tubing 30 is spaced inwardly from proximal end 18 and is also spaced inwardly from the surrounding portion of housing 14. Projecting outwardly from housing 14 is a peg 32 which is located approximately adjacent the proximal end of inner tubing 30.

Depicted in FIGS. 2, 3, 4, and 6 is the other, female connector member 40 of two part connector assembly 10. Connector member 40 includes an elongate housing 42 with a bore 44 therethrough. Housing 42 has a proximal end 46 and a distal end 48. Located at distal end 48 of housing 14 is an adapter 50 to which a tube 52 is attached as shown in FIG. 4. As with adapter 22, adapter 50 is sized to receive whatever sized tube 52 desired.

Figure 1:
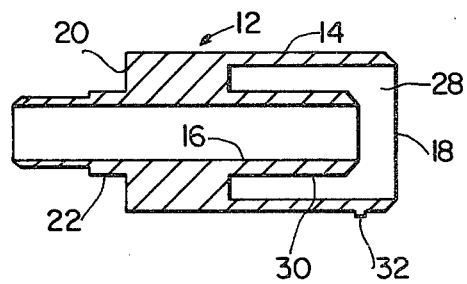
FIG. 1 is a cross-sectional plan view of one connector member of the connector assembly of the present invention.
Figure 2:
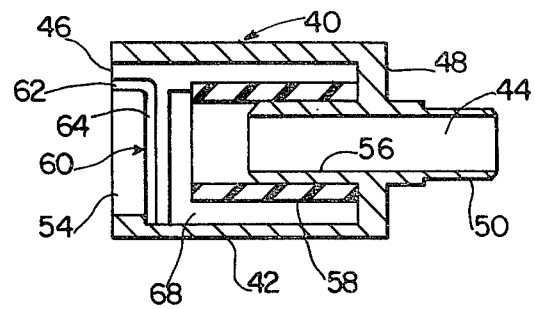
FIG. 2 is a cross-sectional plan view of the other connector member of the connector assembly of the present invention.
Figure 3:
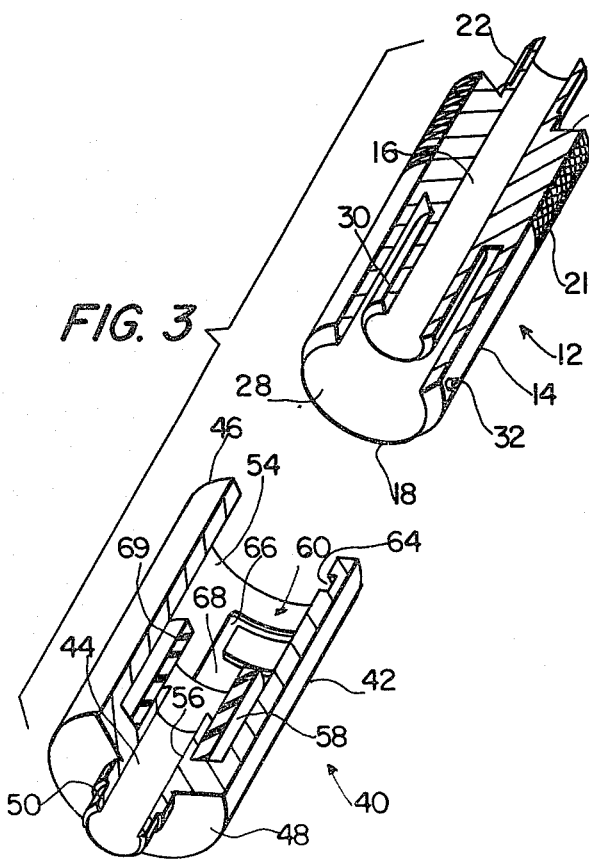
FIG. 3 is a partially cutaway prespective view of the unconnected connector members of the present invention.

Proximal end 46 of housing 42 is provided with an annular opening 54 as shown best in FIGS. 2 and 3. Located in annular opening 54 is a sterile inner tubing 56. Inner tubing 56 is spaced inwardly from proximal end 46 and is also spaced inwardly from the surrounding portion of housing 42. Located around inner tubing 56 is a cover tubing 58. Cover tubing 58 extends longitudinally beyond inner tubing 56. It should be noted that cover tubing 58 is spaced inwardly of proximal end 46 of housing 42 and is also spaced inwardly from the surrounding portion of housing 42.

Located adjacent proximal end 46 of housing 42 is an exit slot 60. Exit slot 60 includes a short longitudinal slot portion 62 formed in proximal end 46. Connected at right angles to the distal end of longitudinal slot portion 62 is a transverse slot portion 64. Transverse slot portion 64 extends approximately one-half of the way around the periphery of housing 42. Connected to the other end of transverse slot portion 64 is a short longitudinal slot portion 66. Longitudinal slot portion 66 connects transverse slot portion 64 with a semi-cylindrical recessed portion 68 provided in housing 42. As shown, the outside, radial wall 69 forms one side of both recessed portion 68 and longitudinal slot portion 66.

In the preferred embodiment of the present invention, connector member 12 is integrally formed of a relatively rigid material such as vinyl plastic. Similarly, connector member 40, with the exception of cover tubing 58, is also integrally formed of a rigid material such as vinyl plastic. Cover tubing 58 of connector member 40 is securely attached by a suitable glue or the like to housing 42 and/or inner tubing 56 and is made of a relatively flexible material which is also preferably vinyl plastic. Where connector assembly 10 is used to connect an autotransfusion device to a thoracotomy tube and to an underwater drainage device, the vinyl plastic chosen must be blood compatible as well.

Figure 6:
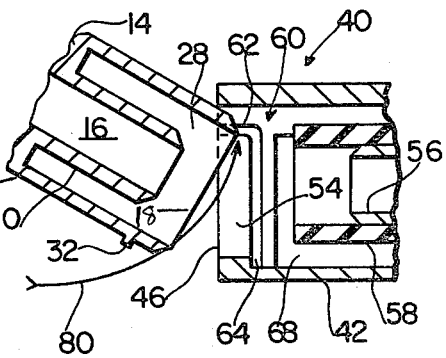
FIG. 6 is a cross-sectional plan view showing the deepest area of penetration of the end of misaligned connector members.

While the overall size of connector assembly 10 is not of particular importance to the present invention, the relative sizes of connector members 12 and 40 are of paramount importance. As shown best in FIGS. 4 and 6, housing 14 is telescopically received in housing 42 with a clearance only sufficient to provide a sliding fit therebetween. Thus, as shown in FIG. 6, proximal end 18 of housing 12 cannot enter annular opening 54 so as to touch and contaminate cover tubing 58. For example, the relative sizes of housing 12 and annular opening 54 can be designed so that proximal end 18 of housing 12 only extends or penetrates into annular opening 54 along line 80 when housing 12 and 40 are not substantially aligned. Also, inner tubing 30 of connector member 12 is telescopically received in cover tubing 58. With cover tubing 58 preferably made of a flexible material, no clearance is provided between cover tubing 58 and inner tubing 30 but instead inner tubing 30 is force fit into cover tubing 58. Thus, the friction fit between cover tubing 58 and inner tubing 30 is preferably also used to hold connector members 12 and 40 together during operation.

The relative longitudinal dimensions of connector members 12 and 40 are also of significant importance. The depth of annular opening 54 on connector member is designed so that as proximal end 18 of housing 14 contacts housing 42, the ends of inner tubings 30 and 56 also contact one another. Thus, upon connection of connector assembly 10, no longitudinal gap is allowed between proximal end 18 of connector member 12 and connector member 40 and between inner tubings 30 and 56 so that a smooth and uninterrupted bath is provided between tubings 30 and 56 for an even flow of liquid between the two.

It should also be appreciated that exit slot 60 prevents the inadvertent separation of connector members 12 and 40 and also prevents connector member 12 and 40 from flying apart and spilling any liquid in inner tubings 30 and 56 during intentional separation. In order to separate connector members 12 and 40, connector member 12 is preferably rotated and pulled longitudinally away from connector member 40. This causes inner tubing 30 to rotate in and pull away from cover tubing 58 in the easiest manner. As soon as inner tubing 58 clears cover tubing 58, connector members 12 and 40 would fly apart under the longitudinal force exerted if not for exit slot 60 and peg 32. Instead, as inner tubing 58 clears cover tubing 58, peg 32 is located in semi-cylindrical recessed portion 68 and limits the further longitudinal movement of connector member 12 to the short distance that is provided at that time between peg 32 and the proximal end of recessed portion 68. Even if peg 32 is located directly in front of longitudinal slot portion 66, the movement of connector member 12 is still limited to this same distance plus the short length of longitudinal slot portion 66. Thus, connector member 12 and 40 cannot fly apart.

In order to separate connector members 12 and 40 after inner tubing 30 is out of cover tubing 58, connector member 12 is rotated relative to connector member 40 until peg 32 contacts radial wall 69. This aligns peg 32 with longitudinal slot portion 66 and a longitudinal force easily moves peg 32 to the end of longitudinal slot portion 66 adjacent the end of transverse slot portion 64. Then, a relative rotation of approximately one-half turn of connector members 12 and 40 in the opposite direction causes peg 32 to travel to the other end of transverse slot portion 64 adjacent longitudinal slot portion 62. A further longitudinal movement of connector member 12 relative to connector member 40 causes peg 32 to exit from longitudinal slot portion 62 and connector members 12 and 40 are free to be completely separated by whatever further longitudinal movement is necessary. Obviously, assembly of connector member 12 and 40 occurs in the reverse manner described for disconnection. It should be noted that semi-cylindrical recessed portion 68 is provided so that during assembly of connector member 12 and 40, peg 32 can move freely in recessed portion 68 whereby connector member 12 and 40 are free to rotate as inner tubing 30 is preferably rotatably inserted into cover tubing 58.

Figure 5:
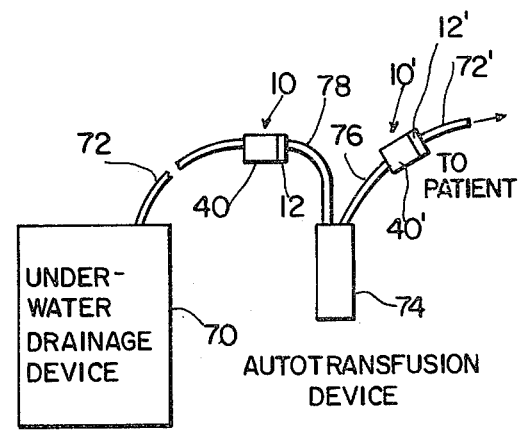
FIG. 5 is a schematic representation of a use of the connector assembly of the present invention.

The operation of connector assembly 10 in a typical application such as depicted in FIG. 5 is as follows. An underwater drainage device 70, such as discussed above, is provided with a thoracotomy suction tube attached to the pleural cavity of the patient. When autotransfusion of the patient is desired, the thoracotomy suction tube is cut into two tubes 72 and 72'. An autotransfusion device 74 having an inlet tube 76 and a suction outlet tube 78 is then appropriately attached to tubes 72 and 72'. Initially, the sterility of tubes 72, 72', 76 and 78 are not affected by their relative connections. However, when it is desired to remove autotransfusion device 74 and substitute a new autotransfusion device, or to remove autotransfusion device 74 and reconnect tube 72 to tube 72', the maintenance of sterility in tubes 72 and 72' becomes a problem. To solve this problem, connector assemblies 10 and 10' are initially provided to connect tubes 72 and 78 and tubes 76 and 72', respectively. This is easily accomplished by attaching tube 72 to adapter 50 of connector member 40 and tube 78 to adapter 22 of connector member 12. Similarly, tube 72' is connected to adapter 22' of connector member 12' and tube 76 is connected to adapter 50' of connector member 40'. It should be appreciated that tubes 72 and 72' must be provided with mating connector members such as connector member 40 and connector member 12'.

When autotransfusion device 74 is filled and a new auto transfusion device 74 is desired, connector member 12 is quickly and easily disconnected from connector member 40 and connector member 40' is easily and quickly disconnected from connector member 12'. The new autotransfusion device 74 is then provided with identical connector members 12 and 40' which are quickly and easily reconnected to connector members 40 and 12', respectively. Obviously, this procedure can be repeated as many times as necessary.

It should be noted that during the connection of connector member 12 to connector member 40, it is inevitable that the outer surface of housing 14 becomes contaminated. However, as inner tubing 30 is completely surrounded by housing 14, neither the inner nor outer surface of inner tubing 30 becomes contaminated during this procedure. After connection of connector number 12 to connector member 40, the contamination present on the outer surface of housing 14 contaminates the inner surface of housing 42. This contamination is contained between housing 14 and housing 42 by reason of the abutting of proximal end 18 of housing 14 against housing 42 as shown in FIG. 4. In addition, if desired, the spread of contamination to inner tubings 30 or 56 can be further prevented by the abutting of cover tubing 58 against housing 14. The lack of longitudinal gaps between connector member 12 and connector member 40 serves to prevent the spread of any contamination found on the outer surface of housing 14.

During a subsequent disconnection of connector member 40 from connector member 12 and the insertion of a new connector member 12, contamination present on the inner surface of housing 42 is prevented from reaching the interior of inner tubing 56 by cover tubing 58.

After reconnection of connection member 12 to connector member 40, it is possible that some contamination may have reached the outer surface of cover tubing 58. In most applications, this will be of little consequence as inner tubings 30 and 56 are not themselves contaminated. However, in the application of the present invention depicted in FIG. 5, suction is being provided so that bores 16 and 44 of connector members 12 and 40, respectively, are under a negative pressure. In such a situation, the provision of a flexible cover tubing 58 having a specified internal diameter becomes important. Thus, as connector member 12 is connected with connector member 40, inner tubing 30 is force fit into flexible cover tubing 58. This provides an airtight seal to prevent any contaminants on the outside of cover tubing 58 from being drawn in and contaminating inner tubings 30 and 56. It should also be noted that the abutting of the ends of inner tubings 30 and 56 against each other also helps to prevent the spread of any contamination.

The use and advantages of connector assembly 10 described above applies as well to the use of connector assembly 10'. As depicted in FIG. 5, when autotransfusion is no longer desired, connector members 12 and 40' are simply disconnected from connector members 40 and 12', respectively. Then, as drainage of the pleural cavity is frequently still desired, connector members 40 and 12' are simply connected together. Again, the sterility of the inner tubings of connector members 40 and 12' is maintained so that no contamination reaches the patient. It should be noted at this time that it is important to provide the ends of tubes 72 and 72' with mating connector members. It should also be noted that because tubes 76 and 78 also are attached to mating connector members 12 and 40', connector members 12 and 40' can be connected to each other to seal autotransfusion device 74 from further contamination through tubes 76 and 78.

In order to simplify use of underwater drainage device 70 and autotransfusion device 74, underwater drainage device 70 including tubes 72 and 72' and connector members 40 and 12' can be initially provided in a sterile package. Similarly, autotransfusion device 74 with tubes 76 and 78 and appropriate connector members 12 and 40' can similarly be initially provided in a sterile package. Thus, when usage of underwater drainage device 70 with or without auto transfusion device 74 is desired, the appropriate connector members are easily and quickly assembled as desired.

It should also be appreciated that connector members 12 and 40 can be held together by another suitable means besides the friction fit between cover tubing 58 and inner tubing 30. For example, one or more additional pegs could be provided near the distal end of connector member 12 with mating spiral or transverse locking grooves provided in connector member 40. With such a connecting means, the friction fit between cover tubing 58 and inner tubing 30 would then have to be only as tight as needed to make the fit airtight.

While the present invention has been described with respect to an exemplary embodiment thereof, it will be understood by those of ordinary skill in the art that these and other variations and modifications may be effected within the scope and spirit of the invention.

What is claimed is:

1. A mating two-part connector assembly for connecting two tubes or the like which prevents the entry of contaminates in the tubes during use and subsequent reuse of one part of the two part connection assembly, the connector assembly comprising:

a reusable first connector member including
an elongate housing having a distal end and a proximal end, said elongate housing further having an elongate opening in the proximal end thereof;
a bore through said elongate housing located coaxially with the longitudinal axis of said housing;
an adapter located around said bore on the distal end of said housing, said adapter being sized to secure one of the tubes thereto; and
a sterile inner tubing located around said bore and inside of said housing, said inner tubing being spaced inwardly from the proximal end of said housing and also spaced inwardly from the surrounding portion of said housing adjacent thereto;

a reusable second connector member including
an elongate housing having a distal end and a proximal end, said elongate housing further having an elongate opening in the proximal end thereof which is sized such that said housing of said second connector member telescopically receives a portion of the proximal end of said housing of said first connector member;
a bore through said elongate housing located coaxially along the longitudinal axis of said housing;
an adapter located around said bore on the distal end of said housing, said adapter being sized to secure the other of the tubes thereto;
a sterile inner tubing located around said bore and inside of said housing, said inner tubing being spaced inwardly from the proximal end of said housing and also spaced inwardly from the surrounding portion of said housing adjacent thereto; and
a cover tubing located around said sterile inner tubing of said second housing and extending outwardly beyond the inwardly spaced end of said inner tubing, said cover tubing further being spaced inwardly from the proximal end of said housing and from the surrounding portion of said housing adjacent thereto such that the proximal end of said first housing cannot contact said cover tubing at any insertion angle and said first housing is spaced from said cover tubing after said first and second connector members have been connected, the portion of said cover tubing extending outwardly from said inner tubing being sized to snuggly and telescopically receive a portion of said inner tubing of said first housing; and a connecting means for separably holding said first connector member and said connector member together such that a portion of said first housing is located inside of said second housing and a portion of said first inner tubing is located inside of said cover tubing and is abutting said second inner tubing and such that after disconnection and a subsequent reuse of one of said connector members with a mating connector member, the sterility of said inner tubing of the one of said connector members is maintained.

2. A connector assembly as claimed in claim 1 wherein said elongate housing, said adapter, and said inner tubing of said first connector member and of said second connector member are integrally formed.

3. A connector assembly as claimed in claims 1 or 2 wherein said elongate housing, said adapter, and said inner tubing of said first connector member and of said second connector member are formed of a relatively rigid material; and wherein said cover tubing is attached securely to said second connector member and said cover tubing is made of a relatively flexible material.

4. A connector assembly as claimed in claim 3 wherein said elongate housing, said adapter, and said inner tubing of said first connector member and of said second connector member are made of a rigid blood compatible vinyl plastic and said cover tubing is made of a flexible blood compatible vinyl plastic.

5. A connector assembly as claimed in claim 3 wherein said connecting means is the friction fit between said cover tubing and said inner tubing of said first housing.

6. A connector assembly as claimed in claim 3 wherein the proximal end of said first housing contacts an inner portion of said second housing which defines the longitudinal distal end of said elongate opening therein and wherein the proximal end of said first inner tubing contacts the proximal end of said second inner tubing as said connecting means holds said connector members together such that a longitudinal gaps exist between said first connector member and said second connector member through which contaminants might pass.

7. A connector assembly as claimed in claim 3 further including a stop means for preventing the direct longitudinal disengagement of said first connector member and said second connector members.

8. A connector assembly as claimed in claim 7 wherein said stop means includes a peg projecting from one of said housings of said first connector member and said second connector member, and an exit slot provided in the other housing of said first connector member and second connector member which receives said peg, said exit slot including a portion having a longitudinal axis not parallal to the longitudinal axis of said other housing such that a relative lateral motion between said first connector member and said second connector member is required before said first connector members and said second connector member can be disengaged.

9. A connector assembly as claimed in claim 8 wherein said housing, said adapter, and said inner tubing of said first connector member and of said second connector member and said cover tubing of said second connector member all have a circular shaped cross section where the cross sections are taken along a section plane perpendicular to the longitudinal axis of said first connector member and said second connector member.

10. A connector assembly as claimed in claim 9 wherein said exit slot includes a first short longitudinal slot portion beginning at the proximal end of said other housing, a lateral slot portion extending at an angle from the distal end of said first short longitudinal slot portion and a second short longitudinal slot portion connected to the other end of said lateral slot portion and extending toward said distal end of said other housing such that a relative rotational and longitudinal movement between said first connector member and said second connector member is required for disengagement.

11. A connector assembly as claimed in claim 10 wherein said other housing includes an elongate cylindrical portion recessed at the same depth of said slot portions extending circumferentially from one side of said second short longitudinal slot portion such that location of said peg in said second short longitudinal slot portion is easily facilitated during disconnection by rotating said first connector members relative to said second connector member until said peg engages the outer longitudinal boundary of said cylindrical portion adjacent said second longitudinal slot portion.

* * * * *